(12) United States Patent
Scheuermann

(10) Patent No.: US 8,224,461 B2
(45) Date of Patent: Jul. 17, 2012

(54) POROUS FIBER ELECTRODE COATING AND RELATED METHODS

(75) Inventor: Torsten Scheuermann, Munich (DE)

(73) Assignee: Cardiac Pacemakers, Inc., St. Paul, MN (US)

( * ) Notice: Subject to any disclaimer, the term of this patent is extended or adjusted under 35 U.S.C. 154(b) by 331 days.

(21) Appl. No.: 12/703,544

(22) Filed: Feb. 10, 2010

(65) Prior Publication Data

US 2010/0241204 A1 Sep. 23, 2010

Related U.S. Application Data

(60) Provisional application No. 61/160,771, filed on Mar. 17, 2009.

(51) Int. Cl.
*A61N 1/00* (2006.01)

(52) U.S. Cl. ........................................ 607/121; 607/116

(58) Field of Classification Search .......... 607/115–128; 600/372–395
See application file for complete search history.

(56) References Cited

U.S. PATENT DOCUMENTS

| | | | |
|---|---|---|---|
| 5,861,023 A | 1/1999 | Vachon | |
| 6,057,031 A | 5/2000 | Breme et al. | |
| 7,310,544 B2 | 12/2007 | Brister et al. | |
| 2006/0036307 A1 | 2/2006 | Zarembo et al. | |
| 2006/0204738 A1 | 9/2006 | Dubrow et al. | |
| 2007/0255378 A1 | 11/2007 | Polkinghorne et al. | |
| 2007/0299491 A1 | 12/2007 | Borgaonkar et al. | |
| 2008/0241512 A1 | 10/2008 | Boris et al. | |
| 2008/0248263 A1 | 10/2008 | Kobrin | |

FOREIGN PATENT DOCUMENTS

| | | |
|---|---|---|
| EP | 0808193 | 11/1997 |
| EP | 0897997 | 2/1999 |
| WO | WO2007003516 A2 | 1/2007 |
| WO | WO2007120442 A2 | 10/2007 |

OTHER PUBLICATIONS

Xinhua Zong, et al., Electrospun fine-textured scaffolds for heart tissue constructs, Biomaterials 26 (2005) 5330-5338, www.sciencedirect.com.
Meiling Liu, et al., Adsorption of bovine serum albumin and fibrinogen on hydrophilicity-controllable surfaces of polypyrrole doped with dodecyl benzene sulfonate—A combined piezoelectric quartz crystal impedance and electrochemical impedance study, Polymer 47 (2006) 3372-3381.
Tasuku Ogawa, et al., Super-hydrophobic surfaces of layer-by-layer structured film-coated electrospun nanofibrous membranes, Nanotechnology 18 (2007), 165607 (8pp).
R. Morent, et al., Non-thermal plasma treatment of textiles, Surface & Coatings Technology 202 (2008), 3427-3449.
Partial International Search Report issued in PCT/US2010/023749, mailed Jul. 19, 2010, 5 pages.
International Search Report and Written Opinion issued in PCT/US2010/023749, mailed Sep. 15, 2010, 17 pages.

*Primary Examiner* — Scott Getzow

(74) *Attorney, Agent, or Firm* — Faegre Baker Daniels LLP

(57) ABSTRACT

The embodiments herein relate to an electrode having a porous coating including a fiber mesh, a multi-layer coating, and an outer coating, and a method of making the same. The various electrode coating embodiments include pores in the coating that prevent access by protein or cells while allowing for ion and/or liquid access.

12 Claims, 7 Drawing Sheets

80

```
┌─────────────────────────────────────────────────────────┐
│ Electrospin the nanofibers onto a cylindrical rod       │─82
└─────────────────────────────────────────────────────────┘

┌─────────────────────────────────────────────────────────┐
│ Remove the mesh from the rod and position on the        │─84
│ electrode                                               │
└─────────────────────────────────────────────────────────┘

┌─────────────────────────────────────────────────────────┐
│ Apply heat to the mesh to shrink it onto the electrode  │─86
└─────────────────────────────────────────────────────────┘

┌─────────────────────────────────────────────────────────┐
│ Dip-coat the electrode and mesh into a TiO₂ colloid     │─88
│ solution                                                │
└─────────────────────────────────────────────────────────┘

┌─────────────────────────────────────────────────────────┐
│ Dip-coat the electrode and mesh into a polyacrylic acid │─90
│ aqueous solution                                        │
└─────────────────────────────────────────────────────────┘

┌─────────────────────────────────────────────────────────┐
│ Repeat the dip-coating steps to form alternating layers │─92
└─────────────────────────────────────────────────────────┘

┌─────────────────────────────────────────────────────────┐
│ Dry the coating at 80° C for 24 hours                   │─94
└─────────────────────────────────────────────────────────┘

┌─────────────────────────────────────────────────────────┐
│ Coat the mesh and inner coating with fluoroalkylsilane  │─96
└─────────────────────────────────────────────────────────┘

┌─────────────────────────────────────────────────────────┐
│ Dry and heat the coating at 80° C for 1 hour            │─98
└─────────────────────────────────────────────────────────┘
```

Fig. 8A

POROUS FIBER ELECTRODE COATING AND RELATED METHODS

CROSS-REFERENCE TO RELATED APPLICATION

This application claims priority under 35 U.S.C. §119 to U.S. Provisional Application No. 61/160,771, filed on Mar. 17, 2009, entitled "Porous Fiber Electrode Coating and Related Methods," which is incorporated herein by reference in its entirety for all purposes.

TECHNICAL FIELD

This invention relates to body implantable medical devices, and more particularly, to coated implantable electrodes for sensing electrical impulses in body tissue or for delivering electrical stimulation pulses to an organ, for example, for pacing the heart.

BACKGROUND

Various types of medical electrical leads for use in cardiac rhythm management systems are known. Such leads are typically extended intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles. At the same time, the leads are exposed to various external forces imposed, for example, by the human muscular and skeletal system, the pulse generator, other leads, and surgical instruments used during implantation and explanation procedures. There is a continuing need for improved lead designs.

SUMMARY

Discussed herein are various porous coatings for implantable medical electrical leads, including porous coatings having a fiber mesh and at least one coating, as well as medical leads including such coatings.

In Example 1, a medical electrical lead comprises a flexible, elongated polymeric lead body, a conducting wire extending through the at least one lumen, a connector coupled to the lead body, an electrode disposed on an exterior portion of the lead body, and a porous coating disposed on the electrode. The lead body defines at least one longitudinal lumen therethrough, and the connector mechanically and electrically couples the lead to an implantable pulse generator device. The electrode is electrically coupled to the conducting wire. The porous coating comprises a polymeric nanofiber mesh; a first coating disposed on the mesh, and a second coating disposed on the first coating. The mesh comprises polyetheretherketone, the first coating comprises $TiO_2$ and polyacrylic acid, and the second coating comprises a fluoroalkylsilane.

Example 2 relates to the medical electrical lead according to Example 1, wherein the first coating is a multi-layer coating comprising layers of $TiO_2$ and polyacrylic acid.

Example 3 relates to the medical electrical lead according to Example 2, wherein the first coating comprises alternating layers of $TiO_2$ and polyacrylic acid.

Example 4 relates to the medical electrical lead according to Example 2, wherein the first coating comprises at least five alternating layers of $TiO_2$ and polyacrylic acid.

Example 5 relates to the medical electrical lead according to Example 1, wherein the porous coating comprises pores, wherein each of the pores has a diameter ranging from about 1 μm to about 5 μm.

Example 6 relates to the medical electrical lead according to Example 1, wherein the polymeric nanofiber mesh is an electro-spun polymeric nanofiber mesh.

Example 7 relates to the medical electrical lead according to Example 1, wherein the polymeric nanofiber mesh is a finely woven polymeric nanofiber mesh.

Example 8 relates to the medical electrical lead according to Example 1, wherein the second coating includes a fluoroalkylsilane selected from the group consisting of a compound having the formula $CF_3(CF_2)_7(CH_2)_2Si(OCH_3)_3$, heptadecafluoro-1,1,2,2-tetrahydrodecyltriethoxysilane, heptadecafluoro-1,1,2,2-tetrahydrodecyltrimethoxysilane, heptadecafluoro-1,1,2,2-tetra-hydrodecyltrichlorosilane, tridecafluoro-1,1,2,2-tetrahydrooctyltrichlorosilane, tridecafluoro-1,1,2,2-tetrahydrooctyltrimethoxysilane, tridecafluoro-1,1,2,2-tetrahydrooctyltriethoxysilane, and trifluoropropyltrimethoxysilane.

In Example 9, a medical electrical lead comprises a flexible, elongated polymeric lead body, a conducting wire extending through the at least one lumen, a connector coupled to the lead body, an electrode disposed on an exterior portion of the lead body, and a porous coating disposed on the electrode. The lead body defines at least one longitudinal lumen therethrough and the connector mechanically and electrically couples the lead to an implantable pulse generator device. The electrode is electrically coupled to the conducting wire. The porous coating comprises a patterned fiber mesh comprising polytetrafluoroethylene and a first coating disposed on the fiber mesh, the first coating comprising a hydrophilic composition.

Example 10 relates to the medical electrical lead according to Example 9, wherein the hydrophilic composition comprises a carbon coating.

Example 11 relates to the medical electrical lead according to Example 9, wherein the hydrophilic composition comprises $TiO_2$ and polyacrylic acid.

Example 12 relates to the medical electrical lead according to Example 9, wherein the porous coating comprises pores, wherein each of the pores has a diameter ranging from about 0.1 μm to about 10 μm.

Example 13 relates to the medical electrical lead according to Example 9, wherein the porous coating comprises pores, wherein each of the pores has a diameter that is less than about 3 μm.

Example 14 relates to the medical electrical lead according to Example 9, wherein the patterned fiber mesh is a woven fiber mesh.

Example 15 relates to the medical electrical lead according to Example 9, wherein the patterned fiber mesh is heat-shrinkable.

Example 16 relates to the medical electrical lead according to Example 9, wherein the patterned fiber mesh comprises a tubular structure.

In Example 17, a method of making an electrode for a medical electrical lead of the type having a lead body and at least one electrical conducting wire comprises forming an electrode on the lead body, disposing a polymeric nanofiber mesh on the electrode, applying a first multi-layer coating to the polymeric nanofiber mesh, and applying a second coating to the first multi-layer coating. The nanofiber mesh comprises polyetheretherketone, the first multi-layer coating comprises layers of $TiO_2$ and polyacrylic acid, and the second coating comprises fluoroalkylsilane.

Example 18 relates to the method according to Example 17, wherein disposing the polymeric nanofiber mesh on the electrode comprises electro-spinning the polymeric nanofiber mesh onto the electrode.

Example 19 relates to the method according to Example 17, wherein the polymeric nanofiber mesh comprises a finely woven polymeric nanofiber mesh.

Example 20 relates to the method according to Example 17, wherein applying the first multi-layer coating to the polymeric nanofiber mesh further comprises coating the electrode and the polymeric nanofiber mesh in the $TiO_2$, coating the electrode and the polymeric nanofiber mesh in the polyacrylic acid, and repeating the two coating steps in alternating sequence at least five times.

In Example 21, a method of making an electrode for a medical electrical lead of the type having a lead body and at least one electrical conducting wire comprises forming an electrode on the lead body, disposing a patterned fiber mesh on the electrode, and applying a first coating to the patterned fiber mesh. The patterned fiber mesh comprises polytetrafluoroethylene and the first coating comprises a hydrophilic composition.

Example 22 relates to the method according to Example 21, the method further comprising weaving a fiber mesh into the patterned fiber mesh using a 2 over 1 weave.

Example 23 relates to the method according to Example 21, wherein the hydrophilic composition comprises a carbon coating, $TiO_2$ and polyacrylic acid, BioSlide™, or a plasma treatment.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 8A is a flow chart of a method of making a lead with a porous coating, according to one embodiment.

DETAILED DESCRIPTION

Figure 1:
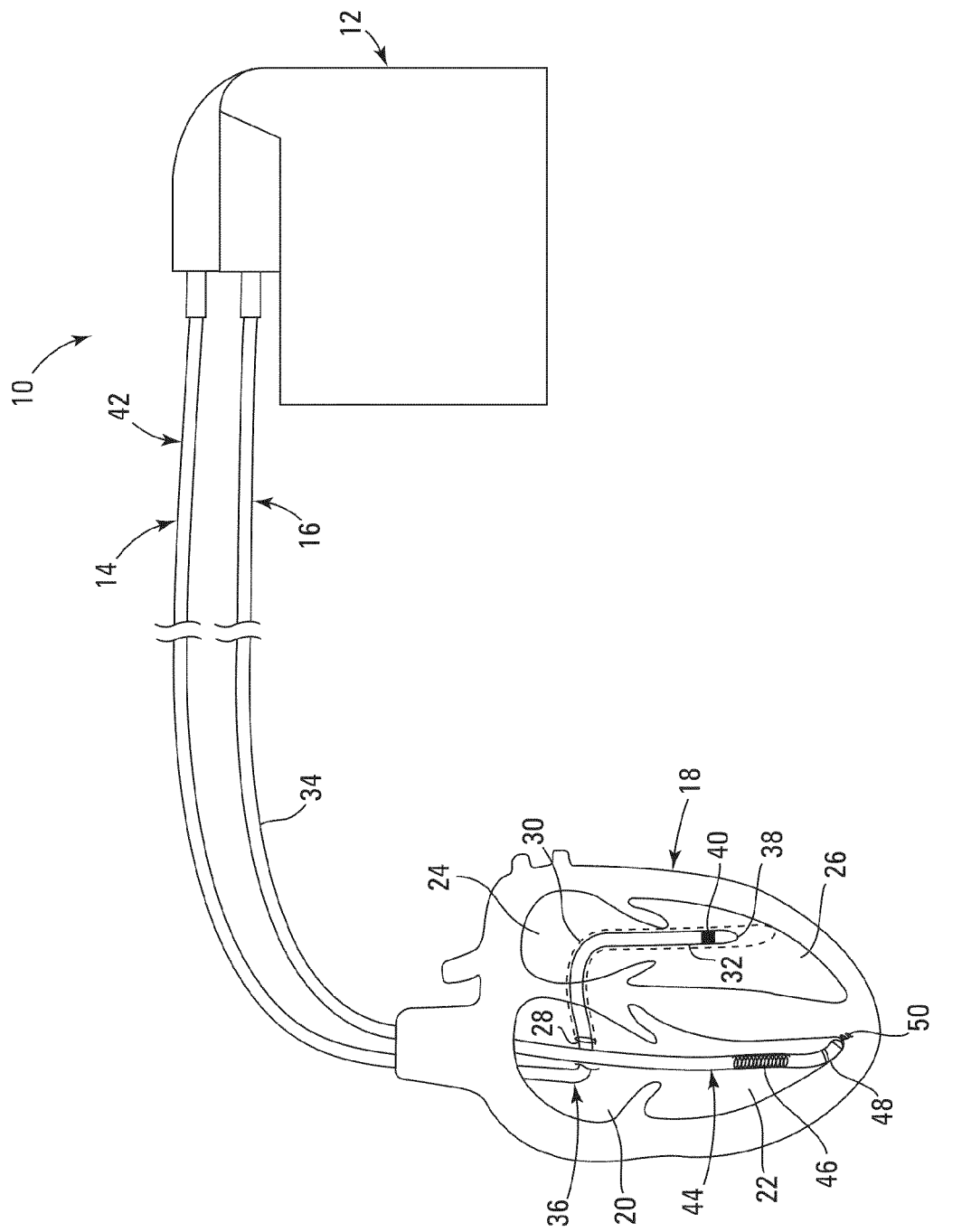
FIG. 1 is a schematic drawing of a cardiac rhythm management system including a pulse generator coupled to a pair of medical electrical leads deployed in a patient's heart, according to one embodiment.

The various embodiments disclosed herein relate to a medical electrical lead having an electrode having a porous coating and related methods of making the lead. The leads according to the various embodiments of the present invention are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardiac defibrillators, and/or cardiac resynchronization therapy (CRT) devices, the medical electrical leads according to embodiments of the invention can be endocardial leads configured to be partially implanted within one or more chambers of the heart so as to sense electrical activity of the heart and apply a therapeutic electrical stimulus to the cardiac tissue within the heart. Additionally, the leads formed according to embodiments of the present invention may be particularly suitable for placement in a coronary vein adjacent to the left side of the heart so as to facilitate bi-ventricular pacing in a CRT or CRT-D system. Still additionally, leads formed according to embodiments of the present invention may be configured to be secured to an exterior surface of the heart (i.e., as epicardial leads). FIG. 1 is a schematic drawing of a cardiac rhythm management system 10 including a pulse generator 12 coupled to a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30.

According to one embodiment, as shown in FIG. 1, lead 14 includes a proximal portion 42 and a distal portion 36, which as shown is guided through the right atrium 20, the coronary sinus ostium 28 and the coronary sinus 30, and into the branch vessel 32 of the coronary sinus 30. The distal portion 36 further includes a distal end 38 and an electrode 40 both positioned within the branch vessel 32. The illustrated position of the lead 14 may be used for delivering a pacing and/or defibrillation stimulus to the left side of the heart 18. Additionally, it will be appreciated that the lead 14 may also be partially deployed in other regions of the coronary venous system, such as in the great cardiac vein or other branch vessels for providing therapy to the left side or right side of the heart 18.

In the illustrated embodiment, the electrode 40 is a relatively small, low voltage electrode configured for sensing intrinsic cardiac electrical rhythms and/or delivering relatively low voltage pacing stimuli to the left ventricle 26 from within the branch coronary vein 32. In various embodiments, the lead 14 can include additional pace/sense electrodes for multi-polar pacing and/or for providing selective pacing site locations.

As further shown, in the illustrated embodiment, the lead 16 includes a proximal portion 34 and a distal portion 44 implanted in the right ventricle 22. In other embodiments, the CRM system 10 may include still additional leads, e.g., a lead implanted in the right atrium 20. The distal portion 44 further includes a flexible, high voltage electrode 46, a relatively low-voltage ring electrode 48, and a low voltage tip electrode 50 all implanted in the right ventricle 22 in the illustrated embodiment. As will be appreciated, the high voltage electrode 46 has a relatively large surface area compared to the ring electrode 48 and the tip electrode 50, and is thus configured for delivering relatively high voltage electrical stimulus to the cardiac tissue for defibrillation/cardioversion therapy, while the ring and tip electrodes 48, 50 are configured as relatively low voltage pace/sense electrodes. The electrodes 48, 50 provide the lead 16 with bi-polar pace/sense capabilities.

In various embodiments, the lead 16 includes additional defibrillation/cardioversion and/or additional pace/sense electrodes positioned along the lead 16 so as to provide multipolar defibrillation/cardioversion capabilities. In one exemplary embodiment, the lead 16 includes a proximal high voltage electrode in addition to the electrode 46 positioned along the lead 16 such that it is located in the right atrium 20 (and/or superior vena cava) when implanted. As will be appreciated, additional electrode configurations can be utilized with the lead 16. In short, any electrode configuration can be employed in the lead 16 without departing from the intended scope of the present invention.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, a cardiac resynchronization (CRT) device configured for bi-ventricular pacing, and/or includes combinations of pacing, CRT, and defibrillation capabilities.

Figure 2:
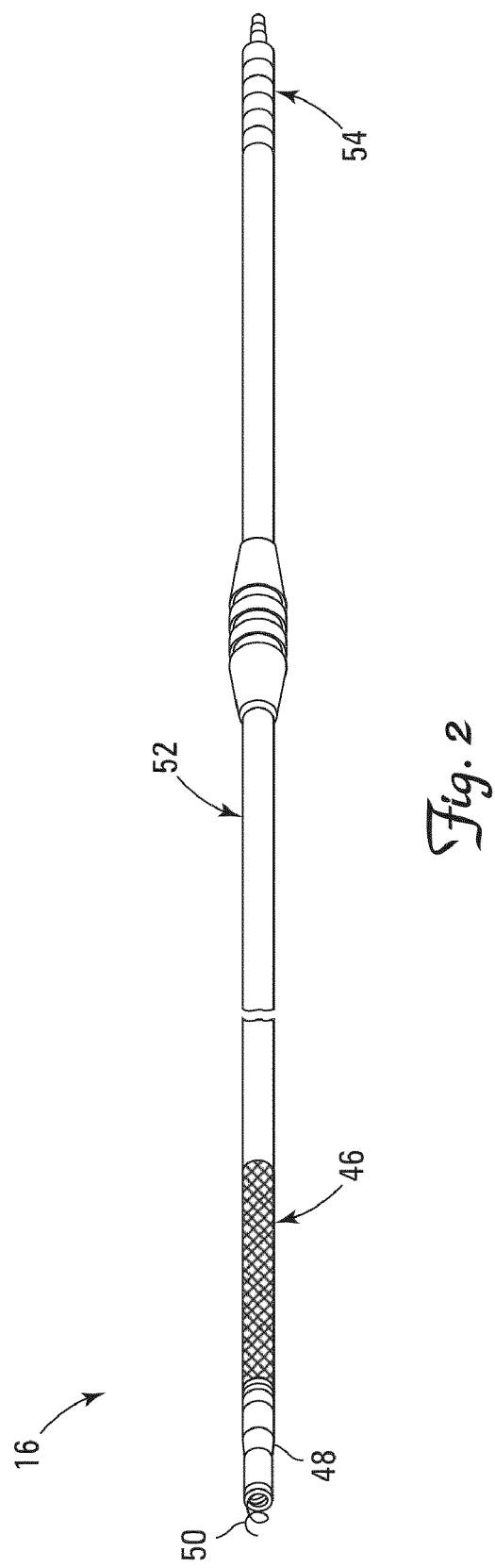
FIG. 2 is a perspective view of one of the leads shown in FIG. 1, according to one embodiment.

FIG. 2 is a perspective view of the lead 16 shown in FIG. 1. As discussed above, the lead 16 is adapted to deliver electrical pulses to stimulate a heart and/or for receiving electrical pulses to monitor the heart. The lead 16 includes an elongated polymeric lead body 52, which may be formed from any polymeric material such as polyurethane, polyamide, polycarbonate, silicone rubber, or any other known polymer for use in this type of lead.

According to one implementation, the polymeric material is stable to a temperature of at least about 100° Celsius. That is, the polymeric material is configured to maintain its integrity up to at least about 100° C. In one aspect, this heat stability allows the polymeric material to withstand the coating processes described below. Alternatively, the polymeric material is stable to a temperature of at least about 70° Celsius.

As further shown, the lead 16 further includes a connector 54 operatively associated with the proximal end of the lead body 52. The connector 54 is configured to mechanically and electrically couple the lead 16 to the pulse generator 12, and may be of any standard type, size or configuration. As will be appreciated, the connector 57 is electrically and mechanically connected to the electrodes 46, 48, 50 by way of one or more conducting wires (not shown) within the lead body 52. The conducting wires utilized may take on any configuration providing the necessary functionality. For example, as will be appreciated, the conducting wires coupling the electrodes 48 and/or 50 to the connector 54 (and thus, to the pulse generator 12) may be coiled conductors defining an internal lumen for receiving a stylet or guidewire for lead delivery. Conversely, in various embodiments, the conducting wire to the high voltage electrode 53 may be a multi-strand cable conductor.

According to the various embodiments of the present invention, one or more of the electrodes 46, 48, 50, e.g., the high voltage electrode 46, includes a porous composite coating that inhibits tissue in-growth and/or attachment to the electrode surface. In one embodiment, the coating inhibits tissue in-growth and/or attachment by preventing blood cell access to the electrode surface as a result of the coating pore sizes. Alternatively, the coating has hydrophobic properties that may inhibit tissue in-growth and/or attachment to the electrode surface. In a further alternative, the coating has small pores that restrict blood cell access to the electrode surface in combination with hydrophilic properties that may allow liquid access to the underlying electrode to enhance the effectiveness of the electrode. Thus, the electrode configurations according to various embodiments of the present invention provide alternatives to existing techniques for inhibiting tissue adhesion and in-growth to electrode surfaces, e.g., ePTFE coatings or wraps.

As will be appreciated, the electrode configurations described herein according to the various embodiments of the present invention may also be utilized for the electrodes of the lead 14 (see FIG. 1) configured for implantation in the coronary venous system, as well as electrodes for other leads such as right atrial and epicardial leads.

Figure 3:
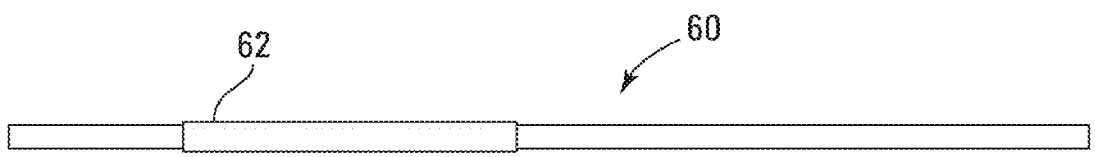
FIG. 3 is a schematic drawing of an electrode having a porous coating, according to one embodiment.

FIG. 3 schematically depicts a lead 60 with an electrode (similar to the electrode in FIGS. 1 and 2) having a porous coating 62. In this embodiment, the porous coating 62 covers or is positioned over the electrode. Alternatively, it is understood that the porous coating can be positioned over not only the electrode, but also other portions of the lead body as well. In one embodiment, the porous coating is positioned over the electrode and also extends beyond the electrode to some portion of the lead body. Alternatively, the porous coating is positioned over the entire length of the lead body. According to one embodiment, a porous coating that covers or is positioned over the electrode and at least some portion of the lead body beyond the electrode can mask a transition portion of the lead body. That is, certain lead bodies have transition portions at which two different segments with different characteristics meet, and those transition portions can include changing diameters or outer surfaces or other characteristics that can contact and potentially damage some portion of the patient's tissues (such as an inner wall of an artery or vein) during insertion or retraction. The porous coating can be used to cover such transition portions and thus protect the patient from the potential damage caused by such portions during insertion or retraction.

According to one implementation, the porous coating 62 has a fiber mesh and a first coating disposed on the mesh. Alternatively, the porous coating 62 has a fiber mesh, a first coating disposed on the mesh, and a second coating disposed on the first coating. For purposes of this application, "porous coating" is intended to mean a fiber mesh in combination with at least one coating disposed on the mesh. "First coating" and "second coating" are intended to mean coatings that are applied to or disposed on the mesh.

In accordance with one embodiment, the fiber mesh is made up of a nanofiber mesh. Alternatively, the fiber mesh is a patterned fiber mesh.

Figure 4:
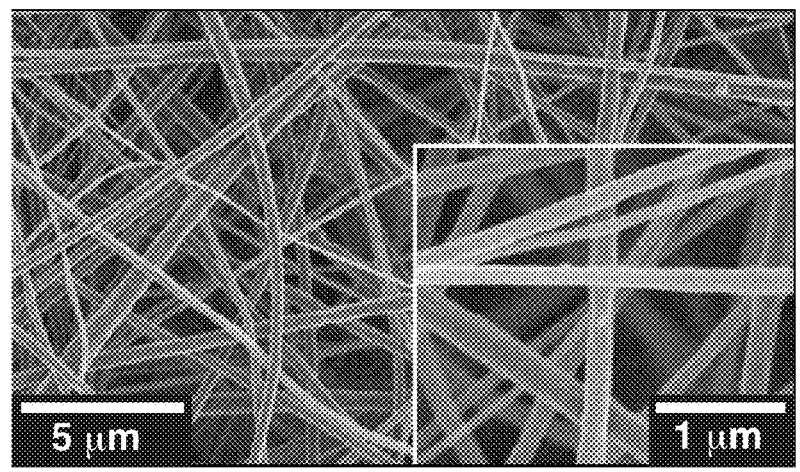
FIG. 4 is an expanded schematic view of a nanofiber mesh, according to one embodiment.

FIG. 4 depicts an exemplary SEM image of one embodiment of a nanofiber mesh. For purposes of this application, the term "nanofiber mesh" is intended to mean any fiber mesh having fibers capable of being formed into an un-patterned or non-uniform mesh to be included in an electrode coating and ranging in diameter from about 10 nm to about 1,000 nm.

In one implementation, the nanofiber mesh is an interlocking, un-patterned arrangement of polymeric nanofibers. The polymeric nanofiber material may include fibers having a diameter ranging from about 10 nm to about 1,000 nm. An exemplary polymeric material from which the nanofiber mesh is derived includes polyetheretherketone ("PEEK"). Alternatively, the nanofibers may be made of polyurethane, polystryrene, polyethylene terephthalate, polymethyl methacrylate, polycarbonate, or any other known polymers that can be used in nanofibers. As described below, the mesh according to one embodiment is created using an electrospinning process in which the fibers are spun into an interlocking arrangement and then positioned on the electrode. Alternatively, the mesh is first woven in a random or un-patterned fashion and then positioned on the electrode.

As mentioned above, in alternative embodiments, the mesh is a patterned fiber mesh. For purposes of this application, the term "patterned mesh" or "patterned fiber mesh" is intended to mean any fiber mesh having fibers capable of being interlaced or otherwise formed into a patterned or non-random arrangement such as a woven pattern or other type of patterned or non-random arrangement to be included in a porous electrode coating.

Figure 5A:
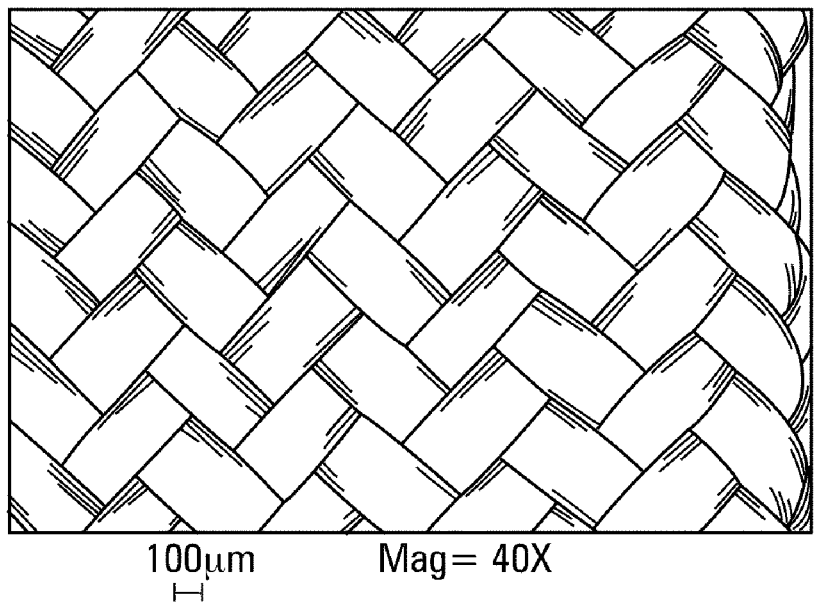
FIG. 5A is an expanded schematic view of a patterned fiber mesh, according to one embodiment.
Figure 5B:
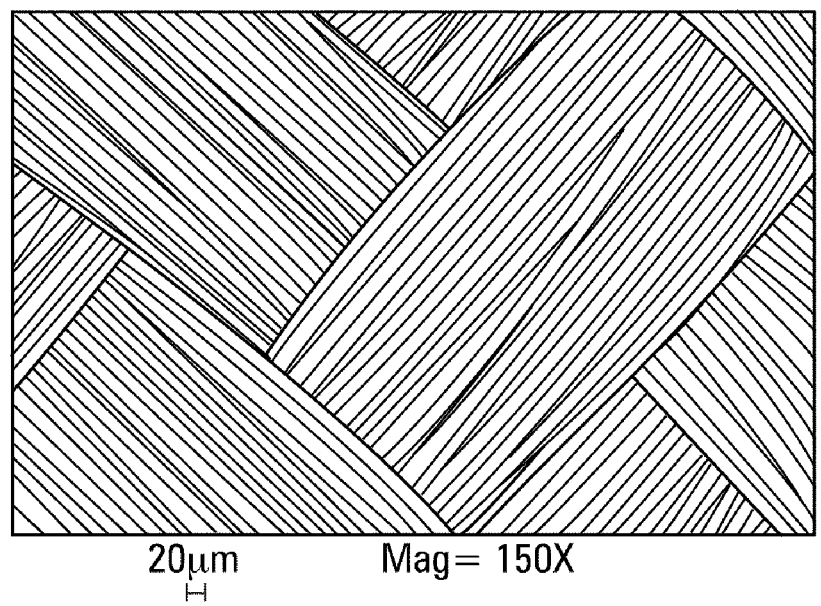
FIG. 5B is a further expanded schematic view of the patterned fiber mesh of FIG. 5A.

In one implementation, the patterned mesh of the porous coating is a woven arrangement of fibers as best shown in FIGS. 5A and 5B, which depict exemplary SEM images of one embodiment of a patterned fiber mesh at 40× magnification (FIG. 5A) and 150× magnification (FIG. 5B). The fibers in the woven mesh can vary in number from about 1 fiber to about 1,000 fiber bundles. In one embodiment, the woven mesh consists of 48 fibers. In one embodiment, the fibers are woven using a "2 over 1" weave or pattern. Alternatively, any known non-random weave or pattern can be used. In a further embodiment, the fibers can be formed into any known patterned or non-random structure. The fibers can have a diameter ranging from about 0.01 µm to about 10 µm.

According to one embodiment, the fibers are made of a heat-shrinkable material such as polytetrafluoroethylene ("PTFE") (also known by its most common brand name: Teflon®). Alternatively, the heat-shrinkable material is polyvinylidene fluoride ("PVDF"). In a further alternative, the material can be any heat-shrinkable material that can be formed into weavable fibers. The heat-shrinkable material, according to one implementation, can be shrunk upon application of heat ranging in temperature from about 120 degrees to about 150 degrees Celsius and can shrink in an amount that is greater than 5% of the original size of the material. In accordance with one embodiment, the heat is applied quickly to avoid heat diffusion into the core of the lead, thereby preventing possible damage to the lead as a result of the heat.

In accordance with an alternative implementation, the fibers can be made of a non-heat-shrinkable material such as polyvinylidene chloride ("PVDC"). Alternatively, the non-heat-shrinkable material can be polyether ether ketone ("PEEK") or carbon fibers or any other non-heat-shrinkable material that can be formed into weavable fibers.

It is understood that the fibers in the patterned mesh can be made of any material—heat-shrinkable or otherwise—that can be formed into a patterned mesh.

Figure 6:
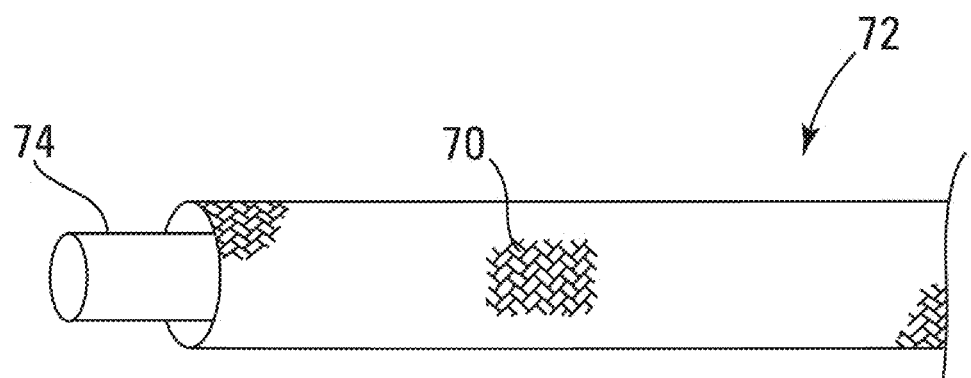
FIG. 6 is a schematic perspective view of a patterned fiber mesh, according to another embodiment.

In accordance with one embodiment as shown in FIG. 6, the patterned mesh 70 is formed into a cylindrical or tubular structure 72 that can be positioned over the electrode 74. In one embodiment, the mesh 70 is formed into the tubular structure 72, positioned over the electrode 74, and then the mesh 70 is heat-shrunk onto the electrode 74. In alternative embodiments in which the material is not heat-shrinkable, the mesh 70 can be attached to the electrode 74 using other methods as described below.

As mentioned above, various embodiments of the porous coatings disclosed herein include a first coating. The first coating coats or is otherwise disposed on the fiber mesh. In one embodiment, the first coating is a coating that includes $TiO_2$ and polyacrylic acid. In a further embodiment, the inner coating is a multi-layered coating having layers of $TiO_2$ and polyacrylic acid. The inner coating can have a number of alternating layers ranging from about 5 layers of $TiO_2$ and 5 layers of polyacrylic acid to about 30 layers of each component.

Alternatively, the first coating includes BioSlide™, a hydrophilic lubricious coating that is commercially available from Boston Scientific SciMed in Minneapolis, Minn. In one embodiment, the BioSlide™ product makes up 100% of the first coating composition. Alternatively, the BioSlide™ product can make up less than 100% of the first coating composition.

In a further alternative, the first coating can be a non-thermal plasma treatment. The non-thermal plasma treatment is a known process of applying a partially-ionized gas with electron temperatures that are higher than ion temperatures, as described in further detail in an article entitled "Non-thermal Plasma Treatment of Textiles" (Surface & Coatings Technology 202 (2008), 3427-3449), which is hereby incorporated herein by reference in its entirety. In one implementation, the non-thermal plasma treatment includes the application of hydrogen/argon or water/argon gas plasma to the fiber mesh under low-pressure ambient temperature conditions. In a further embodiment, the fiber mesh is PTFE, and the application of the hydrogen/argon or water/argon gas plasma increases the wettability of the PTFE fibers.

The first coating, according to another implementation, is a carbon coating such as Cardient® HydroX, which is available commercially from NTTF Coatings GmbH, located in Rheinbreitbach, Germany. Alternatively, the carbon coating can be a diamond-like carbon ("DLC") coating. In certain aspects, the DLC coating is doped with nitrogen or phosphorus. In accordance with certain embodiments, a DLC coating can increase wettability. The carbon coating can make up 100% of the first coating composition. Alternatively, the carbon coating can make up less than 100% of the first coating composition.

According to one implementation, the first coating can be a hydrophilic coating that provides or enhances the hydrophilic nature of the resulting porous coating.

Certain embodiments of the porous coatings disclosed herein have only a first coating. However, as mentioned above, alternative embodiments can include a second coating. In those embodiments that have a second coating, the second coating coats or is otherwise disposed on the first coating and/or fiber mesh. In one embodiment, the second coating is a fluoroalkylsilane ("FAS"). For example, in one implementation the FAS has the following formula: $CF_3(CF_2)_7(CH_2)_2Si(OCH_3)_3$. Further exemplary fluoroalkylsilanes include heptadecafluoro-1,1,2,2-tetrahydrodecyltriethoxysilane, heptadecafluoro-1,1,2,2-tetrahydrodecyltrimethoxysilane, heptadecafluoro-1,1,2,2-tetra-hydrodecyltrichlorosilane, tridecafluoro-1,1,2,2-tetrahydrooctyltrichlorosilane, tridecafluoro-1,1,2,2-tetrahydrooctyltrimethoxysilane, tridecafluoro-1,1,2,2-tetrahydrooctyltriethoxysilane, and trifluoropropyltrimethoxysilane. In accordance with one implementation, the outer coating creates a water contact angle (WCA) that is large enough to further enhance the hydrophobicity of the porous coating. For example, the WCA in one exemplary embodiment is greater than 150°, thereby resulting in a porous coating that is particularly hydrophobic.

Figure 7:
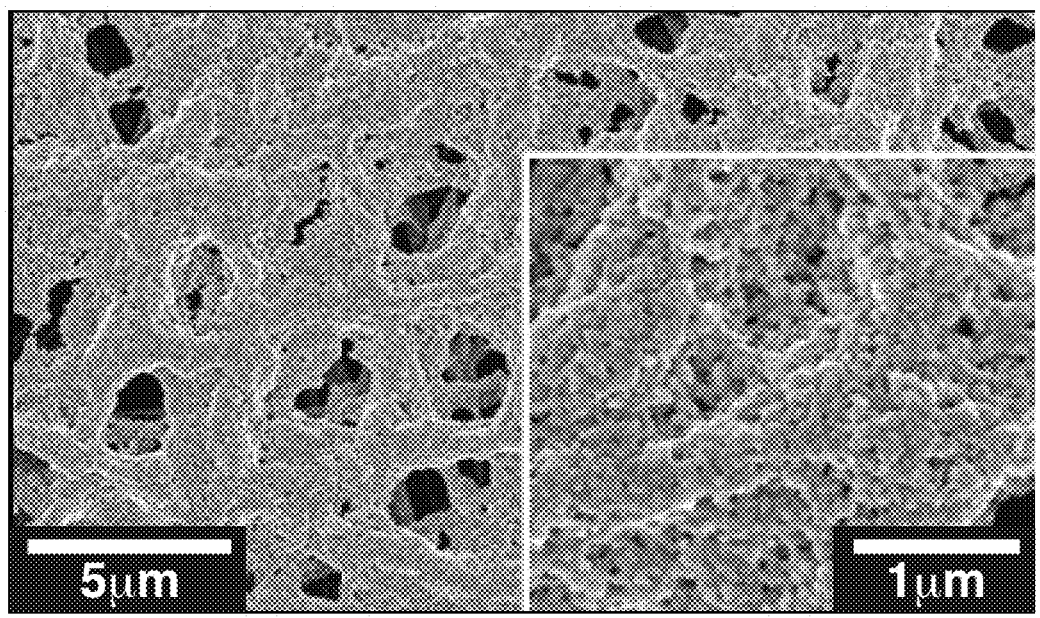
FIG. 7 is an expanded schematic view of a porous coating, according to one embodiment.

Certain specific exemplary embodiments will now be discussed. In one exemplary embodiment, the porous coating has a nanofiber mesh, a first coating, and a second coating that results in a porous coating similar to that depicted in the exemplary SEM image of FIG. 7. In accordance with various embodiments, a porous coating 62 with a nanofiber mesh and two coatings can have pores ranging in diameter from about 1 µm to about 5 µm. The pore size inhibits access of protein and cells, such as red blood cells or any other kind of cells, to the electrode surface while providing ion and moisture access to that surface. Thus, the porous coating 62 is a protein and cell-repelling coating that allows ion and fluid access to the electrode surface. Alternatively, the porous coating 62 with the nanofiber mesh is a hydrophobic coating (and therefore protein and cell-repelling) that allows ion access to the electrode surface.

According to alternative exemplary implementations in which the porous coating 62 has a patterned mesh and a first coating, the porous coating 62 can have a thickness ranging from about 1 to about 500 µm. Alternatively, the thickness of the coating can be less than 150 µm. In accordance with one embodiment, the porous coating 62 with the patterned mesh and first coating has pores ranging in diameter from about 0.1 µm to about 10 µm. Alternatively, the pores are less than about 3 µm. In one implementation, the pore density is greater than about 5% of the total surface area of the porous coating.

Another implementation relates to methods of making an electrode having a porous coating similar to the various embodiments disclosed above. The process can include coating an electrode body according to various embodiments as set forth in detail below.

Figure 8B:
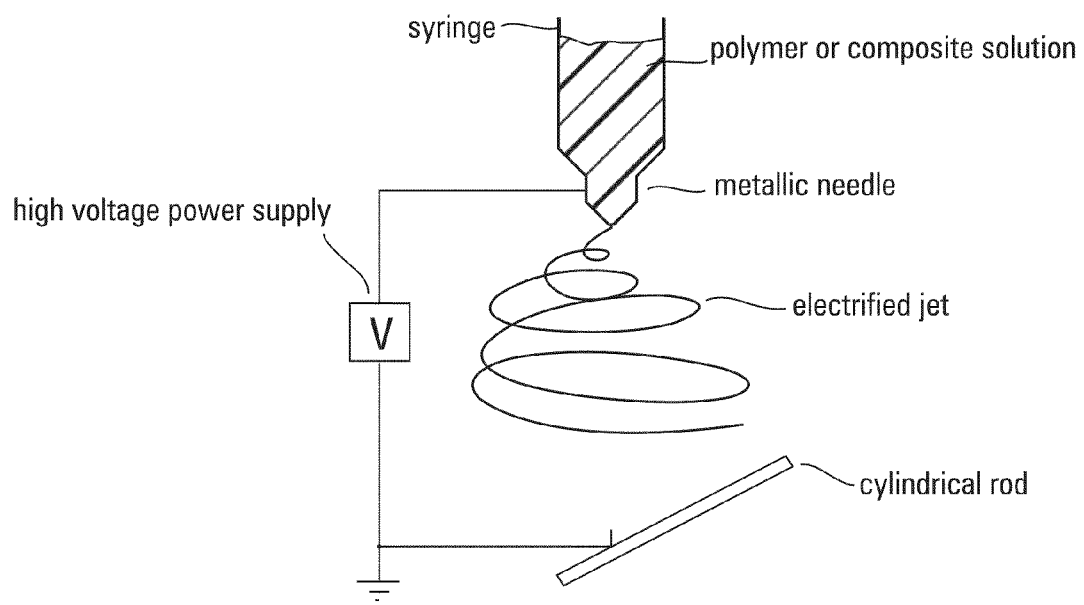
FIG. 8B is a schematic drawing of an exemplary apparatus for electrospinning the nanofibers into a mesh, according to one embodiment.

FIG. 8A sets forth a method for forming a porous coating having a fiber mesh on an electrode 80, according to one embodiment. In one variation in which the fiber mesh is a nanofiber mesh, the nanofiber mesh is created by electrospinning the nanofibers onto a cylindrical rod (block 82), or alternatively, directly onto the electrode body. One apparatus for performing such an electrospinning process is shown schematically in FIG. 8B. Alternatively, the nanofiber mesh can be created by forming a finely woven nanofiber mesh.

In an alternative embodiment in which the fiber mesh is a patterned fiber mesh, the patterned mesh having a tubular structure is created by arranging the fibers into a non-random or patterned form. According to one implementation, the fibers are woven together into a pattern such as that shown in FIGS. 5A and 5B. Alternatively, the fibers can be arranged in any known non-random fashion.

Returning to FIG. 8A, the mesh is then removed from the cylindrical rod and positioned on the electrode (block 84). For heat-shrinkable embodiments, a heating or tempering process is then performed to heat the mesh and thereby shrink it onto the electrode (block 86), which helps to fix or attach the mesh to the electrode. The application of heat can be accomplished using a heat fan, infrared radiation, a laser or lasers, an oven, or any other known heat source for shrinking a heat-shrinkable material.

Next, the electrode and mesh are coated with the first coating. In one embodiment, the electrode and mesh are dip-coated into a $TiO_2$ colloid solution (block 88). Alternatively, the electrode and mesh are coated in $TiO_2$ by any known coating method. According to one embodiment, the coating process is a chemical vapor deposition ("CVD") process. Next, the electrode and mesh are dip-coated into a polyacrylic acid aqueous solution (block 90). Alternatively, the electrode and mesh are coated in polyacrylic acid by any known coating method.

In this embodiment, these coating steps are then repeated multiple times each (block 92), resulting in a combination of $TiO_2$ and polyacrylic acid that, in certain embodiments, can result in alternating layers of $TiO_2$ and polyacrylic acid. In one implementation, the coating steps can be repeated about 30 times each. Alternatively, the coating steps can be repeated any number of times ranging from about 5 to about 30 times each. The resulting coating is then dried at 80° C. for about 24 hours (block 94). Alternatively, the coating can be dried at a temperature ranging from about 30° C. to about 120° C. for a time period ranging from about 1 hour to about 30 hours.

In an alternative implementation, the first coating can be any coating described above. Further, the first coating can alternatively be applied using an atomic layer deposition ("ALD") process. In another embodiment, the outer coating can be applied using any known process that allows for deposition of coating material in locations along a device that are not easily accessible.

As described above, some alternative embodiments contemplated herein have a second coating. In one implementation of such embodiments, the mesh and first coating created above is coated with a second coating. In one embodiment, the second coating is fluoroalkylsilane ("FAS") (block 96). The resulting outer coating is then dried and heated at 80° C. for about 1 hour (block 88). Alternatively, the coating can be dried and heated at a temperature ranging from about 30° C. to about 120° C. for a time period ranging from about 1 hour to about 24 hours.

In alternative embodiments, the coating process can be performed on the fibers prior to the formation of the mesh and/or the tubular structure. In a further embodiment, the coating process can be performed on the mesh after the mesh has been positioned in the appropriate location on a lead body. In embodiments in which the mesh is heat-shrinkable, the coating process can be performed either before or after the mesh is shrunk onto the lead body as described below.

Once the mesh has been coated with the first coating (and, in alternative embodiments, with the second coating), the resulting porous coating can be positioned on the lead body. According to one embodiment in which the mesh is heat-shrinkable, the porous coating is positioned on the lead body and then heat is applied to the coating to shrink it onto the lead in the desired location.

According to one embodiment, the heat is applied along the entire length of the porous coating. Alternatively, the heat can be applied only at certain points along the length of the porous coating and the fixation at those points can be sufficient to maintain the attachment of the coating to the lead body. For example, in those embodiments in which the porous coating covers more of the lead body than just the electrode, the heat can be applied to the ends of the coating and at the electrode itself.

In alternative implementations in which the mesh is not heat-shrinkable, the porous coating can be attached to the lead body in other ways. In one embodiment, the coating can be attached to the lead body with an adhesive. Alternatively, the coating can be attached using a ring that is positioned over a portion of the coating such that the coating is attached between the lead body and the ring.

The scope of the invention is not meant to be limited in application only to leads for implantation in coronary veins. Application of the disclosed embodiments may also be made to right sided bradycardia or tachycardia leads, or epicardial leads. For coronary venous applications, the disclosed embodiment may also be utilized on a non-electrode portion of the lead body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical electrical lead comprising:
   a flexible, elongated polymeric lead body defining at least one longitudinal lumen therethrough;
   a conducting wire extending through the at least one lumen;
   a connector coupled to the lead body for mechanically and electrically coupling the lead to an implantable pulse generator device;
   an electrode disposed on an exterior portion of the lead body, wherein the electrode is electrically coupled to the conducting wire; and
   a porous coating disposed on the electrode, the porous coating comprising:
      a polymeric nanofiber mesh comprising polyetheretherketone;
      a first coating disposed on the fiber mesh, comprising $TiO_2$ and polyacrylic acid; and
      a second coating disposed on the first coating, comprising a fluoroalkylsilane.

2. The lead of claim 1, wherein the first coating is a multi-layer coating comprising layers of $TiO_2$ and polyacrylic acid.

3. The lead of claim 2, wherein the first coating comprises alternating layers of $TiO_2$ and polyacrylic acid.

4. The lead of claim 2, wherein the first coating comprises at least five alternating layers of $TiO_2$ and polyacrylic acid.

5. The lead of claim 1, wherein the porous coating comprises pores, wherein each of the pores has a diameter ranging from about 1 μm to about 5 μm.

6. The lead of claim 1, wherein the polymeric nanofiber mesh is an electro-spun polymeric nanofiber mesh.

7. The lead of claim 1, wherein the polymeric nanofiber mesh is a finely woven polymeric nanofiber mesh.

8. The lead of claim 1, wherein the second coating includes a fluoroalkylsilane selected from the group consisting of a compound having the formula $CF_3(CF_2)_7(CH_2)_2Si(OCH_3)_3$, heptadecafluoro-1,1,2,2-tetrahydrodecyltriethoxysilane, heptadecafluoro-1,1,2,2-tetrahydrodecyltrimethoxysilane, heptadecafluoro-1,1,2,2-tetra-hydrodecyltrichlorosilane, tridecafluoro-1,1,2,2-tetrahydrooctyltrichlorosilane, tridecafluoro-1,1,2,2-tetrahydrooctyltrimethoxysilane, tridecafluoro-1,1,2,2-tetrahydrooctyltriethoxysilane, and trifluoropropyltrimethoxysilane.

9. A method of making an electrode for a medical electrical lead of the type having a lead body and at least one electrical conducting wire therein, the method comprising:
   forming an electrode on the lead body;
   disposing a polymeric nanofiber mesh on the electrode, the nanofiber mesh comprising polyetheretherketone;
   applying a first multi-layer coating to the polymeric nanofiber mesh, the first multi-layer coating comprising layers of $TiO_2$ and polyacrylic acid; and
   applying a second coating to the first multi-layer coating, the second coating comprising fluoroalkylsilane.

10. The method of claim 9, wherein disposing the polymeric nanofiber mesh on the electrode comprises electrospinning the polymeric nanofiber mesh onto the electrode.

11. The method of claim 9, wherein the polymeric nanofiber mesh comprises a finely woven polymeric nanofiber mesh.

12. The method of claim 9, wherein applying the first multi-layer coating to the polymeric nanofiber mesh further comprises:
   coating the electrode and the polymeric nanofiber mesh in the $TiO_2$;
   coating the electrode and the polymeric nanofiber mesh in the polyacrylic acid; and
   repeating the two coating steps in alternating sequence at least five times.

* * * * *